United States Patent [19]

Mizukami et al.

[11] Patent Number: 5,714,627
[45] Date of Patent: Feb. 3, 1998

[54] METHOD FOR PREPARING AROMATIC CARBONATE

[75] Inventors: Masamichi Mizukami; Takuo Ohshida; Hiroaki Ohgi; Hidefumi Harada, all of Ibaraki, Japan

[73] Assignee: Mitsubishi Gas Chemical Company, Inc., Tokyo, Japan

[21] Appl. No.: 703,885

[22] Filed: Aug. 27, 1996

[30] Foreign Application Priority Data

Aug. 28, 1995 [JP] Japan ................... 7-218948
Feb. 26, 1996 [JP] Japan ................... 8-038264
Feb. 26, 1996 [JP] Japan ................... 8-038265
Feb. 26, 1996 [JP] Japan ................... 8-038266
May 23, 1996 [JP] Japan ................... 8-128478

[51] Int. Cl.$^6$ ................................. C07C 68/06
[52] U.S. Cl. .................... 558/274; 558/270; 558/271
[58] Field of Search ........................ 558/270, 271, 558/274

[56] References Cited

U.S. PATENT DOCUMENTS 4,533,504  8/1985  Bolon et al. ................... 260/463
5,543,546  8/1996  Tsuneki et al. ................ 558/270

FOREIGN PATENT DOCUMENTS 0 685 455 A1  12/1995  European Pat. Off. ........ C07C 69/96
5-507060      10/1993  Japan ..................... C07C 69/96

Primary Examiner—Michael G. Ambrose
Attorney, Agent, or Firm—Sughrue, Mion, Zinn, Macpeak & Seas, PLLC

[57] ABSTRACT

A process for producing an aromatic carbonate which comprises: reacting a dialkyl carbonate represented by general formula (1) with an aromatic carboxylic acid aryl ester represented by general formula (2) in the presence of a catalyst to produce an aromatic carbonate represented by one or both of general formulae (3) and (4):

$$R\text{—OCOO—}R \quad (1)$$

$$Ar'\text{—COO—}Ar \quad (2)$$

$$Ar\text{—OCOO—}R \quad (3)$$

$$Ar\text{—OCOO—}Ar \quad (4)$$

wherein R represents an alkyl group having from 1 to 4 carbon atoms, and Ar and Ar' each represents an unsubstituted phenyl group or a phenyl group substituted by a substituent selected from the group consisting of alkyl, alkoxy, aryl, aryloxy and a halogen atom.

17 Claims, No Drawings

METHOD FOR PREPARING AROMATIC CARBONATE

FIELD OF THE INVENTION

The present invention relates to a method for preparing aromatic carbonates. In more detail, the present invention relates to a method for preparing aromatic carbonates having at least one aromatic group by an ester-exchange reaction with a dialkyl carbonate ester. The aromatic carbonate is useful as a raw material for aromatic polycarbonates using a molten ester exchange method.

BACKGROUND OF THE INVENTION

Conventionally, aromatic carbonates have been prepared by reacting aromatic hydroxy compounds with phosgene. However, phosgene is extremely toxic and highly corrosive to an apparatus. In addition, a large amount of alkali is necessary for neutralizing the hydrogen chloride produced as a by-product. Thus, there is a need in the art for development of a method which does not use phosgene, and several proposals have been made. For example, one such method involves oxidatively carbonylating aromatic hydroxy compounds using carbon monoxide and oxygen.

However, in this method, expensive palladium is used as a main catalyst. Furthermore, a co-catalyst, a drying agent, an oxidizing agent, etc., are required. Thus, the reaction system is very complex. Furthermore, the recovery of the catalyst is difficult, and the present state of the art is that yield and production rate have not been achieved at an industrial level.

Another method which involves ester exchange of an aromatic hydroxy compound with an aliphatic carbonate ester has also been known. For example, a method in which lewis acids are used as a catalyst is described in examined Japanese Patent Publication Sho 56-42577, and a method in which lewis acids and proton acids are used as a catalyst is described in unexamined published Japanese Patent Application Sho 60-173016. However, in both of these methods, the reaction time is long, such as from five to twenty-four hours, and the yield is unsatisfactory.

Furthermore, unexamined published Japanese Patent Application No. Sho 54-48733 discloses a method in which a tin compound is used as a catalyst. However, according to this method, despite the reaction time is more than thirty hours, satisfactory yield has not been obtained.

Although similar reactions are disclosed in unexamined published Japanese Patent Application Nos. Sho 57-176932, Sho 60-169444, Sho 56-25138 and Hei 1-265064, etc., the problem of a slow reaction rate has not been solved.

The improvement of reaction rate is very important in industrial applications in order to obtain high production efficiency.

In order to increase the reaction rate, unexamined published Japanese Patent Application Nos. Sho 51-105032 and Sho 56-123948 propose the use of phenyl acetate instead of phenol. Although, phenyl acetate is expensive, however, the industrial use of methyl acetate which is formed as a by-product is not indicated.

In view of the above, U.S. Pat. No. 4,533,504 proposes a method in which phenyl acetate, a raw material, is recycled by converting methyl acetate to ketene and then reacting with phenol. Similarly, unexamined published Japanese Patent Application No. Hei 5-507060 based on a PCT application proposes a method in which phenyl acetate is recycled by reacting methyl acetate with carbon monoxide to produce acetic anhydride, and then reacting with phenol. However, in both of these methods, the step of recycling phenyl acetate is complex and is industrially impractical.

Furthermore, in a conventional method, reaction distillation is conducted under pressure. The reaction is conducted to remove low-boiling compounds (methanol or methyl acetate, etc.) which are produced as by-products. However, dialkyl carbonate, a raw material, is also removed from the reaction system and cannot be utilized efficiently. Furthermore, although it is necessary to separate the extracted mixture of the low-boiling compound as a by-product and dialkyl carbonate, this separation is usually difficult to achieve.

Two methods have been proposed for obtaining an aromatic carbonate by ester exchange from dialkyl carbonate. A first such method involves reacting a dialkyl carbonate with phenol, and a second such method involves reacting a dialkyl carbonate with phenyl acetate.

This is because it was previously considered necessary to remove low-boiling compounds (e.g., by-products such as methanol or methyl acetate) from the system.

That is, in conventional methods, it is necessary to conduct the reaction under pressure, and to remove the low-boiling compounds (by-products), together with dialkyl carbonate (raw material).

SUMMARY OF THE INVENTION

The present invention solves the above-noted problems of the prior art. That is, the present invention provides a new reaction species which replaces phenyl acetate, as well as a method of easily converting the alkyl ester thus produced into an aryl ester.

According to the present invention, dialkyl carbonate and a carboxylic acid aryl ester are reacted in the presence of a catalyst, and it is not necessary to remove the low-boiling compounds (by-products). Thus, dialkyl carbonate (raw material) remains in the reaction system so that it can be utilized efficiently. Furthermore, the present invention eliminates the need to separate the low boiling compounds from dialkyl carbonate. Thus, the present invention provides a method that is much simpler than conventional methods.

As a result of extensive studies, the present inventors discovered that a high reaction rate can be obtained by using aromatic carboxylic acid aryl ester as a reaction species in place of phenyl acetate, and that an aromatic carboxylic acid alkyl ester (by-product) can easily be converted into an aromatic carboxylic acid aryl ester (i.e., one of the raw materials). The present invention has been accomplished based on these findings.

That is, the above objectives have been achieved by providing a method for preparing an aromatic carbonate, which comprises reacting a dialkyl carbonate represented by general formula (1) with an aromatic carboxylic acid aryl ester represented by general formula (2) in the presence of a catalyst to produce an aromatic carbonate represented by one or both of general formulae (3) and (4):

  R—OCOO—R  (1)

  Ar'—COO—Ar  (2)

  Ar—OCOO—R  (3)

  Ar—OCOO—Ar  (4)

wherein R represents an alkyl group having from 1 to 4 carbon atoms, Ar and Ar' each represents an unsubstituted phenyl group or a phenyl group substituted by a substituent selected from the group consisting of alkyl, alkoxy, aryl, aryloxy and a halogen atom.

In a preferred embodiment, the present invention comprises producing an aromatic carboxylic acid aryl ester represented by general formula (2) by reacting an aromatic carboxylic acid alkyl ester represented by general formula (5) and an aromatic hydroxy compound represented by general formula (6) in the presence of a catalyst:

wherein Ar, Ar' and R have the same meanings as indicated above.

In another preferred embodiment, the present invention comprises using an aromatic carboxylic acid alkyl ester, which is a by-product of the reaction of the compounds represented by general formulae (1) and (2), as the reactant represented by general formula (5).

According to the present invention, an aromatic carboxylic acid alkyl ester which is a by-product of the reaction of dialkyl carbonate and an aromatic carboxylic acid aryl ester, is converted into an aromatic carboxylic acid aryl ester (i.e., one of the raw materials) by reacting with an aromatic hydroxy compound. Accordingly, the aromatic carboxylic acid alkyl ester can be recycled. This recycling is very important for industrial applications.

The aromatic carboxylic acid alkyl ester has a carbonyl group that is directly bonded to an aromatic ring and therefore is chemically stable. Accordingly, even if the aromatic carboxylic acid alkyl ester is recycled, it is substantially stable under normal reaction conditions such that no change in properties occurs.

According to the present invention, an aromatic carbonate is easily produced with a sufficient reaction rate and without producing low boiling compounds. Furthermore, the aromatic carboxylic acid alkyl ester by-product) can be easily converted into an aromatic carboxylic acid aryl ester (a raw material). By combining these reactions, an aromatic carbonate can be produced without generating a by-product in all steps. Thus, the present invention has great industrial significance.

DETAILED DESCRIPTION OF THE INVENTION

The present invention is explained in greater detail below.

The aromatic carbonate is produced by reacting an aliphatic carbonate represented by general formula R—OCOO—R (1) with an aromatic carboxylic acid aryl ester represented by general formula Ar'—COO—Ar (2). This reaction is conducted in two stages. That is, substituent R of aliphatic carbonate represented by general formula R—OCOO—R (1) is ester exchanged with the substituent Ar of the aromatic carboxylic acid aryl ester represented by general formula Ar'—COO—Ar (2). As a result, an aromatic aliphatic carbonate represented by general formula Ar—OCOO—R (3) is produced, and at the same time an aromatic carboxylic acid alkyl ester represented by general formula Ar'—COO—R (5) is produced as a by-product. Next, substituent R of the aromatic aliphatic carbonate represented by general formula Ar—OCOO—R (3) is ester exchanged with the substituent Ar of the aromatic carboxylic acid aryl ester represented by general formula Ar'—COO—Ar (2). As a result, the aromatic carbonate represented by general formula Ar—OCOO—Ar (4) is produced, and at the same time an aromatic carboxylic acid alkyl ester represented by general formula Ar'—COO—R (5) is produced as a by-product.

Suitable aromatic aliphatic carbonates represented by general formula R—OCOO—R (1) for use in the present invention include carbonates where the substituent R is an alkyl group having from 1 to 4 carbon atoms. Examples thereof include dimethyl carbonate, diethyl carbonate and isomers of dipropyl carbonate, isomers of dibutyl carbonate. Dimethyl carbonate is preferred from an industrial viewpoint.

Suitable aromatic carboxylic acid aryl esters represented by general formula Ar'—COO—Ar (2) for use in the present invention include aromatic carboxylic acid aryl esters where substituents Ar and Ar' each represents an unsubstituted phenyl group or a phenyl group substituted by a substituent selected from the group consisting of an alkyl group, an alkoxy group, an aryl group, an aryloxy group and a halogen atom. Examples thereof include phenyl benzoate, phenyl o-methylbenzoate, phenyl m-methylbenzoate or phenyl p-methylbenzoate, phenyl 2,4-dimethylbenzoate, phenyl 3,4-dimethylbenzoate, phenyl 3,5-dimethylbenzoate, phenyl 4-n-propylbenzoate, phenyl 4-isopropylbenzoate, phenyl 4-n-butylbenzoate, phenyl 4-isobutylbenzoate, phenyl 4-sec-butylbenzoate, phenyl 4-methoxybenzoate, phenyl 4-phenylbenzoate, phenyl 4-phenoxybenzoate, phenyl 4-chlorobenzoate, phenyl 2,4-dichlorobenzoate, 4-chlorophenyl o-methylbenzoate, 4-phenoxyphenyl 2,6-dimethylbenzoate, etc.

Suitable aromatic carbonates represented by general formula Ar—OCOO—R (3) for use in the present invention include aromatic carbonates where the substituent Ar is an unsubstituted phenyl group or a phenyl group substituted by a substituent selected from the group consisting of an alkyl group, an alkoxy group, an aryl group, an aryloxy group and a halogen atom. Also, the substituent R is an alkyl group having from 1 to 4 carbon atoms. Examples thereof include methyl phenyl carbonate, ethyl phenyl carbonate, n-propyl phenyl carbonate, isopropyl phenyl carbonate, n-butyl phenyl carbonate, isobutyl phenyl carbonate, tert-butyl phenyl carbonate, methyl p-methylphenyl carbonate, methyl o-methylphenyl carbonate, methyl m-methylphenyl carbonate, ethyl p-methylphenyl carbonate, ethyl o-methylphenyl carbonate, ethyl m-methylphenyl carbonate, methyl 2,4-dimethylphenyl carbonate, methyl 3,4-dimethylphenyl carbonate, methyl 3,5-dimethylphenyl carbonate, ethyl 2,4-dimethylphenyl carbonate, ethyl 3,4-dimethylphenyl carbonate, ethyl 3,5-dimethylphenyl carbonate, methyl 4-methoxyphenyl carbonate, methyl 4-phenylphenyl carbonate, methyl 4-phenoxyphenyl carbonate, methyl 4-chlorophenyl carbonate, methyl 2,4-dichlorohenyl carbonate, etc.

Suitable aromatic carbonates represented by general formula Ar—OCOO—Ar (4) for use in the present invention include aromatic carbonates where the substituent Ar is an unsubstituted phenyl group or a phenyl group substituted by a substituent selected from the group consisting of an alkyl group, an alkoxy group, an aryl group, an aryloxy group and a halogen atom. Examples thereof include diphenyl carbonate, di(2-methylphenyl)carbonate, di(3-methylphenyl)carbonate, di(4-methylphenyl)carbonate, di(2-ethylphenyl)carbonate, di(3-ethylphenyl)carbonate, di(4-ethylphenyl)carbonate, bis(2,4-dimethylphenyl) carbonate, bis(3,4-dimethylphenyl)carbonate, bis(3,5-dimethylphenyl)carbonate, di(4-n-propylphenyl)carbonate, di(4-isopropylphenyl)carbonate, di(4-n-butylphenyl) carbonate, di(4-isobutylphenyl)carbonate, di(4-tertbutylphenyl)carbonate, di(4-phenylphenyl)carbonate, di(4-methoxyphenyl)carbonate, di(4-ethoxyphenyl)carbonate, di(4-phenoxyphenyl)carbonate, di(4-chlorophenyl)carbonate, di(2,4-dichlorophenyl)carbonate, etc.

The substituent R of the aromatic carboxylic acid alkyl ester represented by general formula Ar'—COO—R (5) has the same meaning as the substituent R of the aliphatic carbonate, a raw material, represented by general formula R—OCOO—R (1). Furthermore, the substituent Ar' of the aromatic carboxylic acid alkyl ester represented by general formula Ar'—COO—R (5) has the same meaning as the substituent Ar' of the aromatic carboxylic acid aryl ester represented by general formula Ar'—COO—Ar (2). That is, in the present specification and in general formulae (1) to (6), the same symbols define the same sets of substituents. Additionally, the aromatic carboxylic acid alkyl ester represented by general formula Ar'—COO—R (5) can be converted into the aromatic carboxylic acid aryl ester represented by general formula Ar'—COO—Ar (2) by the method described hereinafter, and the aromatic carboxylic acid part of the aromatic carboxylic acid alkyl ester, a by-product, is not substantially consumed.

The aromatic carboxylic acid aryl ester represented by general formula Ar'—COO—Ar (2) is produced by reacting the aromatic carboxylic acid alkyl ester represented by general formula Ar'—COO—R (5) with the aromatic hydroxy compound represented by general formula Ar—OH (6). That is, the substituent R of the aromatic carboxylic acid alkyl ester represented by general formula Ar'—COO—R (5) is ester exchanged by the substituent Ar of the aromatic hydroxy compound represented by general formula Ar—OH (6). As a result, the aromatic carboxylic acid aryl ester represented by general formula Ar'—COO—Ar (2) is produced, and at the same time, an alkyl alcohol is produced as a by-product.

Suitable aromatic carboxylic acid alkyl esters represented by general formula Ar'—COO—R (5) for use as a raw material in producing the aromatic carboxylic acid aryl ester represented by general formula Ar'—COO—Ar (2) in accordance with the present invention may be an aromatic carboxylic acid alkyl ester where the substituent Ar' is an unsubstituted phenyl group or a phenyl group substituted by a substituent selected from the group consisting of an alkyl group, an alkoxy group, an aryl group, an aryloxy group and a halogen atom, and the substituent R is an alkyl group having from 1 to 4 carbon atoms. Examples thereof include methyl benzoate, ethyl benzoate, isomers of propyl benzoate, isomers of butyl benzoate, methyl o-methylbenzoate, methyl m-methylbenzoate, methyl p-methylbenzoate, ethyl o-methylbenzoate, ethyl m-methylbenzoate, ethyl p-methylbenzoate, methyl 2,4-dimethylbenzoate, methyl 3,4-dimethylbenzoate, methyl 3,5-dimethylbenzoate, ethyl 2,4-dimethylbenzoate, ethyl 3,4-dimethylbenzoate, ethyl 3,5-dimethylbenzoate, methyl o-ethylbenzoate, methyl m-ethylbenzoate, methyl p-ethylbenzoate, ethyl o-ethylbenzoate, ethyl m-ethylbenzoate, ethyl p-methylbenzoate, methyl p-n-propylbenzoate, methyl p-isopropylbenzoate, methyl p-n-butylbenzoate, methyl p-isobutylbenzoate, methyl p-tert-butylbenzoate, ethyl p-n-propylbenzoate, ethyl p-isopropylbenzoate, ethyl p-n-butylbenzoate, ethyl p-isobutylbenzoate, ethyl p-tert-butylbenzoate, methyl p-phenylbenzoate, methyl p-methoxybenzoate, methyl p-phenoxybenzoate, methyl p-chlorobenzoate and methyl 2,4-dichlorobenzoate, etc.

Suitable aromatic hydroxy compounds represented by general formula Ar—OH (6) for use as a raw material in producing the aromatic carboxylic acid aryl ester represented by general formula Ar'—COO—Ar (2) in accordance with the present invention may be any aromatic hydroxy compound where the substituent Ar is an unsubstituted phenyl group or a phenyl group substituted by a substituent selected from the group consisting of an alkyl group, an alkoxy group, an aryl group, an aryloxy group and a halogen atom. Examples thereof include phenol, o-cresol, m-cresol, p-cresol, 2,4-dimethylphenol, 3,4-dimethylphenol, 3,5-dimethylphenol, o-ethylphenol, m-ethylphenol, p-ethylphenol, p-n-propylphenol, p-isopropylphenol, p-n-butylphenol, p-isobutylphenol, p-tert-butylphenol, p-phenylphenol, anisole, p-phenoxyphenol, p-chlorophenol, 2,4-dichlorophenol, etc.

The present method can be envisioned as comprising two steps, that is, (A) a carbonate production step, and (B) an aromatic carboxylic acid aryl ester production step. In both steps, the type of reactor is not particularly limited. That is, the reaction may be conducted both in a batch reactor and in a continuous reactor.

When the reaction is conducted in a batch reactor, the (A) carbonate production step, and (B) aromatic carboxylic acid aryl ester production step may be conducted either in the same reactor or in different reactors.

When the reaction is conducted in a continuous reactor, the reaction steps may be carried out either in a fluidized bed, a fixed bed or a stirred-tank reactor. Also, the reaction may be carried out in a multi-stage distillation tower.

The (A) carbonate production step is described below.

In this step a dialkyl carbonate and an aromatic carboxylic acid aryl ester are heated in the presence of a catalyst. The reaction temperature for use in the present invention may be in a wide range of from 50° C. to 300° C., preferably from 90° C. to 240° C. Furthermore, the reaction may be conducted either at atmospheric pressure or under an elevated pressure. The reaction is preferably conducted under pressure, because this allows the reaction to be conducted at higher temperatures. Accordingly, a reactor having pressure resistance properties is preferable, however, the type of reactor is not particularly limited. That is, the reactor may be a batch reactor or a continuous reactor. When a batch reactor is used, the reactor may be a simple reactor which is capable of carrying out the reaction under pressure, heat and agitation. When a continuous reactor is used, a tube extrusion type or agitator type reactor is preferred.

The reaction time varies depending upon the reaction conditions. Usually, the reaction is conducted in the range of from several minutes to several hours, preferably from 30 minutes to 6 hours. Because the present reaction is an equilibrium reaction, it is preferable to allow sufficient reaction time to reach equilibrium (residence time in case of a continuous reaction). However, from an economical view point, it is possible to stop the reaction prior to reaching equilibrium.

The molar ratio of the dialkyl carbonate to the aromatic carboxylic acid aryl ester is not particularly limited. However, a ratio of 0.2 to 50 moles of the dialkyl carbonate per mole of the aromatic carboxylic acid aryl ester is preferred. In this case, it is possible to selectively produce the alkyl aryl carbonate by using a large molar ratio of dialkyl carbonate to the aromatic carboxylic acid aryl ester. Furthermore, when the object is to obtain diaryl carbonate, it is possible to add an alkyl aryl carbonate in advance. In such case, the alkyl aryl carbonate is added in an amount of from 0.1 mole to 10 moles, preferably from 0.1 mole to 1 mole, more preferably from 0.2 to 0.5 mole per mole of the aromatic carboxylic acid aryl ester.

The desired aromatic carbonate can be obtained from the reaction mixture of the above-described method according to the usual separation procedures. When the alkyl aryl carbonate is not needed, it can be returned to the reaction mixture for use as a raw material for producing diaryl carbonate. The alkyl aryl carbonate can be converted into diaryl carbonate using a known disproportionation reaction as described, for example, in unexamined published Japanese Patent Application Sho 58-48537.

Next, the (B) aromatic carboxylic acid aryl ester production step is described below.

In this reaction, the equilibrium is extremely favored toward the original system. Thus, it is necessary to remove alkyl alcohol that is produced in the reaction from the reaction system in order to proceed with the reaction. Therefore, when the present reaction is conducted in a batch reactor, the use of a reactor including a distillation tower having from 1 to 10 stages or more at the upper part of the reactor is preferred. Either of the following two methods may be used. The first is a method in which the alkyl alcohol is selectively removed by reactive distillation. After some extent of the alkyl alcohol is selectively removed by reactive distillation, the reaction is then completed by removing a mixture of the aromatic hydroxy compound and the alkyl alcohol. The second is a method in which the reaction is conducted by removing an aromatic hydroxy compound and alkyl alcohol as a mixture from the time of the start of the reaction.

Once the reaction is complete, the aromatic carboxylic acid aryl ester can be separated by a general method such as distillation, extraction or recrystalization, as needed, after removing the excess aromatic hydroxy compound and the unreacted aromatic carboxylic acid alkyl ester. Furthermore, when the aromatic carbonate is produced in the same reactor, the reaction can be continued by adding dialkyl carbonate, without separation, after removing the excess aromatic hydroxy compound and unreacted aromatic carboxylic acid alkyl ester.

When the present reaction is conducted semi-continuously or continuously, an ordinary continuous reactor, such as a fluidized bed, fixed bed, stirred-tank and multi-stage distillation tower reactor can be used. However, the stirred-tank type reactor and the multi-stage distillation tower reactor are preferred because it is necessary to remove the alkyl alcohol from the reaction system in order to proceed with the reaction. When the stirred-tank type reactor is used, a reactor having a distillation tower provided at the upper part of the reactor may be used.

The distillation tower is not necessary provided at the upper part of the reactor, but may be connected to the reactor via pipes.

When the present reaction is conducted in a distillation tower, the reaction may be conducted by supplying a catalyst and raw materials into the distillation tower; continuously removing alkyl alcohol produced as a by-product from the top of the tower; and continuously removing the reaction mixture containing the catalyst and aromatic carboxylic acid aryl ester from bottom of the tower.

A suitable distillation tower for use in the present invention may be any distillation tower having at least two distillation stages and which is capable of continuous distillation. The number of stages means the number of trays in the case of a tray tower, and the theoretical stage number in the case of a packed column or other distillation tower. Examples of the distillation tower include a tray type distillation tower, such as a bubble cap tray, sieve tray and valve tray; a packed column type distillation tower packed, for example, with Rachig ring, Coil pack, Pall ring, Berl saddle, Cannon packing, Dixon packing, McMahon packing, Hell pack, Sulzer packing, Mellapak, etc. Furthermore, a distillation tower having both packed and tray portions is preferably used.

When a homogeneous catalyst is continuously supplied into the tower, the catalyst and the raw materials may be packed at the same time. This is done by mixing either or both of the aromatic carboxylic acid alkyl ester and aromatic hydroxy compound (raw material), and the catalyst may be supplied in a stage that is different from the stage in which the raw materials are supplied. Furthermore, the catalyst may be supplied at any position that is at least more than one stage from the bottom of the tower. However, the catalyst is preferably supplied within the area from the tower top to the raw material supply position. This is because the reaction usually proceeds within the area below the catalyst supply position.

When a heterogeneous catalyst is used, the catalyst may be supplied at any position in the tower in a necessary amount. The theoretical stage in which the catalyst is present may be more than one stage, and is preferably at least two stages.

This solid catalyst has the effect of introducing a packing into the distillation tower. Furthermore, in those areas where the catalyst is not present, the distillation tower can be used to carry out ordinary functions such as concentration of a reaction product.

The method for continuously supplying the aromatic carboxylic acid alkyl ester and the aromatic hydroxy compound into the distillation tower is not particularly limited. Any method may be used as long as these reactants are supplied so as to contact the catalyst in an area of at least one stage, and preferably two or more stages. That is, the aromatic carboxylic acid alkyl ester and the aromatic hydroxy compound may be supplied to a number of stages of the multi-stage distillation tower as needed so as to satisfy the above condition. Furthermore, the aromatic carboxylic acid alkyl ester and the aromatic hydroxy compound may be supplied to the same stage of the distillation tower or to different stages, respectively.

In the present invention, the alkyl alcohol (low boiling compound) produced by reaction in a continuous multi-stage distillation tower may be removed from the distillation tower in a gaseous state. In this case, the gaseous substance thus removed may be the alkyl alcohol alone or a mixture with the raw materials, and may further contain a high boiling compound in a small amount.

The gaseous substance containing a low boiling compound is removed from a continuous multi-stage distillation tower preferably at a point between the raw material supply position and the tower top, more preferably at the tower top. This is because the concentration of the low boiling product increases in proportion as the distance to the tower top decreases. The gaseous component thus removed may be condensed by cooling, and a part may be returned to the upper part of the distillation tower in a reflux operation. In this reflux operation, an unnecessary increase in reflux ratio is not preferred because excessive heat energy is consumed. Thus, the reflux ratio is usually from 0 to 20, preferably from 0 to 10.

The aromatic carboxylic acid aryl ester produced according to the present invention is continuously removed in a liquid state as a high boiling product from lower part of the continuous multi-stage distillation tower. In this case, the liquid thus recovered may be a high boiling product alone or a mixture with the raw materials, or may contain a small amount of a low boiling product. When the high boiling catalyst can be solved in the reaction mixture under the reaction conditions, the recovered liquid may contain the catalyst. The liquid containing the high boiling product is removed from a lower part of the tower, particularly preferably from the bottom of the tower. A part of the liquid substance thus removed may be returned in a gaseous or gas-liquid mixed condition to the lower part of the distillation tower by heating with a reboiler.

The reaction time (residence time in case of a continuous reaction) varies depending upon the reaction conditions and the reaction method. However, the reaction time is usually from 0.001 to 10 hours, preferably from 0.05 to 6 hours.

The mole ratio of the aromatic carboxylic acid alkyl ester to the aromatic hydroxy compound in accordance with the method of the present invention is in the range of from 20:1 to 1:20. When either one is used in excess, the reaction rate is large. However, this is not preferable because it is then necessary to remove excess raw materials once the reaction is complete.

The reaction may be conducted at a temperature in the range from the boiling point of the alcohol by-product to about the boiling point of the hydroxy compound (e.g., from about 60° C. to about 250° C.) when the reaction is carried out at atmospheric pressure. However, the reaction is preferably conducted at a temperature that is as high as possible (e.g., from 170° C. to 250° C.), because the reaction then proceeds at a faster rate. Furthermore, it is also preferable to carry out the reaction under elevated pressure, and in this case it is preferable to carry out the reaction at a temperature of from 170° C. to 300° C.

The present method comprises (A) a carbonate preparation step, and (B) an aromatic carboxylic acid aryl ester preparation step. The reaction of both steps is an ester exchange reaction such that the same catalyst can be used. To simplify the operation, the catalyst used in the carbonate preparation step and the aromatic carboxylic acid aryl ester preparation step are preferably the same, even though different catalysts may be used.

The ester exchange catalyst for use in the present invention includes one of an alkoxide, an aryloxide, an alkyl substituted oxide and an acetyl acetonate of a metal selected from the group consisting of titanium, aluminum, gallium, tin and yttrium or an adduct thereof with another compound.

Among the catalysts described above, a titanium compound represented by Ti(OX)4 (where X is an alkyl group having from 1 to 4 carbon atoms, or an aryl group), or an adduct of the titanium compound represented by Ti(OX)$_4$.XOH (where X is alkyl group having from 1 to 4 carbon atoms, or an aryl group) is particularly preferred.

Examples of the catalyst include, for example, titanium tetramethoxide, titanium tetraethoxide, titanium tetra-n-propoxide, titanium tetraisopropoxide, titanium tetra-n-butoxide, titanium tetra-sec-butoxide, titanium tetra-tert-butoxide, titanium tetraphenoxide, titanium tetra(4-methylphenoxide), titanium tetrakis(2,4-dimethylphenoxide), titanium tetrakis(3,5-dimethylphenoxide), titanium tetra(4-methoxiphenoxide) and titanium tetra(4-chlorophenoxide).

Examples of the other catalyst include, for example, aluminum trimethoxide, aluminum triethoxide, aluminum tri-n-propoxide, aluminum triisopropoxide, aluminum tri-n-butoxide, aluminum triphenoxide, aluminum tri(4-methylphenoxide), aluminum tri(2,4-dimethylphenoxide), aluminum tri(4-methoxiphenoxide), aluminum tri(4-chlorophenoxide), aluminum acetylacetnate; gallium trimethoxide, gallium triethoxide, gallium tri-n-propoxide, gallium triisopropoxide, gallium tri-n-butoxide, gallium triphenoxide, gallium tri(4-methylphenoxide), gallium tris (2,4-dimethylphenoxide), gallium tri(4-methoxiphenoxide), gallium tri(4-chlorophenoxide); di-n-butyldimethoxytin, di-n-butyldi-n-buthoxytin, di-n-butylethoxytin, tri-n-butylmethoxytin, di-n-butyltin oxide, yttrium acetylacetonate, etc.

As the other ester exchange catalyst, a lewis acid, a proton acid (an organic acid or an inorganic acid) and a mixture of these acids may be used. Examples of the lewis acid include a metal alkoxide, a metal aryloxide, and a metal acetylacetonate (for example, iron triisopropoxide, iron acetylacetonate, triisopropoxyvanadium oxide, lanthanum acetylacetonate, etc.). Examples of the inorganic acid include hydrochloric acid, hydrobromic acid, sulfuric acid, phosphoric acid, etc. Examples of the organic acid include methanesulfonic acid, trifluoromethansulfonic acid, toluenesulfonic acid, benzenesulfonic acid, etc.

Other than the catalysts described above, a basic catalyst, such as sodium hydroxide, potassium hydroxide, calcium hydroxide, sodium carbonate, potassium carbonate and disodium phenyl phosphate; a solid catalyst, such as silica, alumina, titania, silicatitania, zinc oxide, zirconium oxide, gallium oxide, zeolite and a rare earth oxide; and a catalyst made by modifying the surface of these solid catalysts may be used in the present invention.

The catalyst in the present invention may be used alone or in combination with another catalyst. Furthermore, the catalyst for use in the present invention includes an alkoxide or an aryloxide catalyst to which metal halide was changed. Furthermore, titanium alkoxide and titanium aryloxide are known to easily form an adduct, such as Ti(OPh)$_4$.PhOH with phenol, alcohol, ketone and amine. These adducts are effective as catalysts in the present invention.

The amount of the catalyst for use in the present invention is not particularly limited. However, in the case of a homogeneous catalyst, in both the carbonate preparation step and aromatic carboxylic acid aryl ester preparation step, the catalyst is used in the range of from 0.001 mole to 5 mole per mole of the aromatic carboxylate (raw material).

In conducting the present invention, an inactive solvent for the reaction can be used. The present invention can also be conducted in the presence of an inactive gas, or under the pressure of an inert gas. Furthermore, as a matter of course, each material used in the present invention is preferably pure. However, substances produced in the reaction may be contaminated by the raw materials. For example, in the aromatic carboxylic acid aryl ester preparation step, the aromatic carboxylic acid aryl ester may become contaminated by the aromatic acid carboxylic alkyl ester. Furthermore, substances used as a raw material in a subsequent step may be contaminated by the raw materials. For example, in the carbonate preparation step, the aromatic hydroxyl compound may be contaminated by the aromatic carboxylic acid aryl ester.

The present invention is illustrated in greater detail below by reference to the following Examples. However, the present invention is not to be construed as being limited thereto.

EXAMPLE 1

Preparation of Phenyl Benzoate

A Claisen head was attached to a flask having an internal volume of 1000 ml, and a receiver having a gage was attached to the Claisen head via a condenser to make a distillation apparatus.

Methyl benzoate 100 g (735 mmole), phenol 553 g (5876 mmole) and titanium tetraisopropoxide 2.1 g (7.4 mmole) were charged to this apparatus and reacted with stirring at 190° C. The reaction was conducted at atmospheric pressure and the methanol thus produced was removed together with phenol by distillation.

After reacting four hours, excess phenol was removed by distillation at atmospheric pressure. Then, the remaining phenol and methyl benzoate (raw materials) were removed by distillation to obtain phenyl benzoate (product). The boiling point thereof was 140° C./4 mmHg, and the yield was 108 g (74% yield in terms of methyl benzoate).

Preparation of Carbonate

Into an autoclave made of SUS316 having an internal volume of 100 ml were charged the above-produced phenyl benzoate 30 g (151 mmole), dimethyl carbonate 6.82 g (75.7 mmole) and titanium tetraisopropoxide 0.43 g (1.51 mmole). The pressure was elevated to 20 kg/cm$^2$ with nitrogen, and the contents were reacted for three hours at 150° C. After completing the reaction, the reaction mixture was analyzed by gas chromatography. As a result, the yield of methyl phenyl carbonate was 19%, and the yield of diphenyl carbonate was 21%. Furthermore, at the same time, methyl benzoate was produced as a by-product with a yield of 40% (the yield was based on phenyl benzoate).

EXAMPLE 2

The same procedures as in Example 1 were used, except that the reaction temperature of the phenyl carbonate preparation step was 210° C. As a result, the yield of methyl phenyl carbonate was 17%, and the yield of diphenyl carbonate was 24%. Furthermore, at the same time, methyl benzoate was produced as a by-product with a yield of 41% (the yield was based on phenyl benzoate).

EXAMPLE 3–8

Phenyl benzoate was synthesized using the same method as in Example 1. Next, into an autoclave made of SUS316 having an internal volume of 100 ml were charged the phenyl benzoate, dimethyl carbonate and titanium tetraisopropoxide in the amounts indicated in the following Table. The pressure was elevated to 20 kg/cm$^2$ with nitrogen, and the contents were reacted at 180° C. for three hours. After completing the reaction, the reaction mixture was analyzed by gas chromatography. The results are shown in the following Table. The yield was based on phenyl benzoate. The abbreviations used in the following Table are explained as follows.
DPC: diphenyl carbonate
MPC: methyl phenyl carbonate
DMC: dimethyl carbonate
PB: phenyl benzoate

| EXAMPLES | PB | DMC | Ti (OPr)$_4$ | MPC | DPC |
|---|---|---|---|---|---|
| 3 | 3.0 g | 43.6 g | 0.043 g | 82% | 1% |
| 4 | 5.5 g | 40.0 g | 0.079 g | 83% | 2% |
| 5 | 5.5 g | 20.0 g | 0.079 g | 73% | 5% |
| 6 | 20.0 g | 18.2 g | 0.29 g | 57% | 12% |
| 7 | 20.0 g | 9.1 g | 0.29 g | 35% | 20% |
| 8 | 40.0 g | 4.5 g | 0.14 g | 8% | 20% |

EXAMPLE 9

Preparation of Phenyl Benzoate

A Dixon packing was charged into a distillation tower having dimensions of 26 mm×500 mm, and a three-necked flask was provided at the bottom thereof to obtain a continuous multi-stage distillation apparatus having a reboiler. Into this apparatus were charged methyl benzoate, phenol and titanium tetraphenoxide (molar ratio of 1/4/0.01). While maintaining the flask and a 200 mm portion of the lower part of the distillation tower at 210° C., a mixture of phenyl benzoate, phenol and titanium tetraphenoxide (molar ratio of 1/4/0.01) was supplied at a rate of 2.0 g/minute at 100 mm position from the top of the tower. At the same time, continuous reaction distillation was conducted by removing the reaction mixture so that there always was a constant amount of liquid in the flask. From the upper part of the tower, gas and liquid containing methanol as a by-product was obtained as a main component. A liquid containing phenyl benzoate (product) was obtained from the flask. The conversion rate of methyl benzoate at steady state three hours after the start of the reaction was 34.5%, and the selectivity of phenyl benzoate was 100%. The reaction distillation was conducted for six hours. The reaction mixture was then distilled to obtain 90 g of phenyl benzoate.

Preparation of Carbonate

Into an autoclave made of SUS316 having an internal volume of 100 ml were charged above-prepared phenyl benzoate 5.64 g (28.4 mmole), dimethyl carbonate 20 g (222 mmole) and titanium tetraphenoxide 0.13 g (0.30 mmole). The pressure was elevated to 20 kg/cm$^2$ with nitrogen, and then the contents were reacted for three hours at 150° C. After completing the reaction, the reaction mixture was analyzed by gas chromatography. As a result, the yield of methyl phenyl carbonate was 75%, and the yield of diphenyl carbonate was 5%. Furthermore, at the same time, methyl benzoate was produced as a by-product with a yield of 80% (the yield is given in terms of phenyl benzoate)

EXAMPLE 10

Phenyl benzoate was synthesized using the same method as in Example 9. Next, into an autoclave made of SUS316 having an internal volume of 100 ml were charged the synthesized phenyl benzoate 30 g (151 mmole), dimethyl carbonate 6.82 g (75.7 mmole) and titanium tetraphenoxide 0.02 g (0.045 mmole). After replacing the air with nitrogen, the autoclave was sealed and the contents were reacted for two hours at 200° C. After completing the reaction, the reaction mixture was analyzed by gas chromatography. As a result, the yield of methyl phenyl carbonate was 15%, and the yield of diphenyl carbonate was 4%. Furthermore, at the same time, methyl benzoate was produced as a by-product with a yield of 19% (the yield is given in terms of phenyl benzoate).

EXAMPLE 11

Preparation of Phenyl p-toluate

A thermometer and Claisen head were attached to a three-necked flask having an internal volume of 500 ml. A receiver having a gage was attached to the Claisen head via a condenser to make a distillation apparatus. Into this apparatus were charged methyl p-toluate 75 g (0.50 mole), phenol 376 g (4.0 mole) and titanium tetraisopropoxide 1.42 g (5.0 mmole). The contents were reacted with stirring in a 190° C. bath. The reaction was conducted at atmospheric pressure for six hours while removing methanol produced in the reaction. Then, the temperature of the bath was elevated to 196° to 198° C., and phenol was removed by distillation in an amount of as much as 150 g. The remaining phenol and methyl p-toluate were removed by distilling under vacuum (85 mmHg). Then, the vacuum pressure was decreased to obtain phenyl p-toluate. The boiling point was 183° to 185° C./18 mmHg, and the product was a slightly yellow colored white solid. The yield was 72.98 g, (69% in terms of methyl p-toluate). The melting point was 74° to 76° C.

Preparation of Carbonate

Into an autoclave made of SUS316 having an internal volume of 100 ml were charged the synthesized phenyl p-toluate 30 g (141 mmole), dimethyl carbonate 6.37 g (70.7 mmole) and titanium tetraisopropoxide 0.80 g (2.83 mmole). The pressure was elevated to 20 kg/cm$^2$ with nitrogen, and the contents were then reacted for three hours at 180° C. After completing the reaction, the reaction mixture was analyzed by gas chromatography. As a result, the yield of methyl phenyl carbonate was 18%, and the yield of diphenyl carbonate was 15%. Furthermore, at the same time, methyl p-toluate was produced as a by-product with a yield of 33% (the yield is given in terms of phenyl p-toluate).

EXAMPLE 12

Phenyl p-toluate was synthesized using the same method as in Example 11. Then, into an autoclave made of SUS316 having an internal volume of 100 ml were charged the synthesized phenyl p-toluate 30 g (141 mmole), methyl phenyl carbonate 7.17 g (47 mmole), dimethyl carbonate 4.24 g (47 mmole) and titanium tetraphenoxide 0.59 g (1.41 mmole). The pressure was elevated to 20 kg/cm$^2$ with nitrogen, and the contents were reacted for three hours at 180° C. After completing the reaction, the reaction mixture was analyzed by gas chromatography. As a result, the yield of diphenyl carbonate was 30 mmole, and the yield was 42% in terms of phenyl p-toluate. Furthermore, methyl phenyl carbonate was detected in an amount of 35 mmole.

EXAMPLE 13

Preparation of Phenyl 2,4-dimethylbenzoate

A Claisen head was attached to a flask having an internal volume of 1000 ml, and a receiver having a gage was attached to the Claisen head via a condenser to make a distillation apparatus. Into this apparatus were charged methyl 2,4-dimethylbenzoate 80 g (487 mmole), phenol 665 g (7065 mmole) and titanium tetraisopropoxide 6.9 g (24.4 mmole). The contents were reacted with stirring at 195° C. in a bath. The reaction was conducted at atmospheric pressure while removing methanol produced in the reaction together with phenol. After reacting for 4 hours, the temperature of the bath was elevated to 200° C., and excess phenol was removed by distillation at atmospheric pressure. The remaining phenol and methyl 2,4-dimethylbenzoate were removed by distillation under vacuum (85 mmHg) to obtain phenyl 2,4-dimethylbenzoate. The boiling point was 152° C./3 mmHg. The yield was 60 g (54% yield in terms of methyl 2,4-Dimethylbenzoate).

Preparation of Carbonate

Into an autoclave made of SUS316 having an internal volume of 100 ml were charged methyl 2,4-dimethylbenzoate 34.2 g (151 mmole) produced above, dimethyl carbonate 6.82 g (75.7 mmole) and titanium tetraisopropoxide 0.43 g (1.51 mmole). The pressure was elevated to 20 kg/cm$^2$ with nitrogen, and the contents were then reacted for two hours at 150° C. After completing the reaction, the reaction mixture was analyzed by gas chromatography. As a result, the yield of methyl phenyl carbonate was 19%, and the yield of diphenyl carbonate was 8%. Furthermore, methyl 2,4-dimethylbenzoate was produced as a by-product with a yield of 27% (the yield is given in terms of phenyl 2,4-dimethylbenzoate).

EXAMPLE 14

Preparation of Phenyl 3,5-Dimethylbenzoate

A liquid reservoir having a volume of 10 ml was attached by pipes to the upper part of an autoclave made of titanium having an internal volume of 500 ml, to make an apparatus capable of condensing part of a gas phase.

Into this autoclave were charged methyl 3,5-dimethylbenzoate 90 g (550 mmole), phenol 207 g (2200 mmole) and titanium tetraphenoxide/phenol adduct 2.8 g (5.5 mmole) in a state such that the phenol was melting. The autoclave was sealed and then cooled with ice. After sufficient cooling, the inner gas was evacuated with a vacuum pump. Then, the contents were heated and reacted for three hours at 230° C. Furthermore, during the reaction, the liquid held in the reservoir was continuously removed with a pump at a rate of 10 g per hour. After cooling, the reaction mixture in the autoclave was separated by distillation to obtain phenyl 3,5-dimethylbenzoate (product) in an amount of 85 g (68% yield in terms of methyl 3,5-dimethylbenzoate). The boiling point was 155° C./2 mmHg, and the melting point was 32° C.

Preparation of Carbonate

Into an autoclave made of SUS316 having an internal volume of 100 ml were charged phenyl 3,5-dimethylbenzoate 34.2 g (151 mmole) which was produced above, dimethyl carbonate 6.82 g (75.7 mmole) and titanium tetraphenoxide/phenol adduct 0.23 g (0.45 mmole). The pressure was elevated to 20 kg/cm$^2$ with nitrogen, and the contents were then reacted for one hour at 200° C. After completing the reaction, the reaction mixture was analyzed by gas chromatography. As a result, the yield of methyl phenyl carbonate was 25%, and the yield of diphenyl carbonate was 20%. Furthermore, methyl 3,5-dimethylbenzoate was produced as a by-product with a yield of 45% (the yield is given in terms of phenyl 3,5-dimethylbenzoate).

The methyl 3,5-dimethylbenzoate was recovered, and could be used as a raw material for preparing phenyl 3,5-dimethylbenzoate.

EXAMPLE 15

Phenyl 3,5-dimethylbenzoate was synthesized using the same method as in Example 14. Then, into an autoclave made of SUS316 having an internal volume of 100 ml were charged the synthesized phenyl 3,5-dimethylbenzoate 34.3 g (151 mmole), dimethyl carbonate 4.57 g (51 mmole), methyl phenyl carbonate 7.61 g (50 mmole) and titanium tetraphenoxide/phenol adduct 0.23 g (0.45 mmole). After replacing the air with nitrogen, the autoclave was sealed and the contents were reacted for two hours at 200° C. After completing the reaction, the reaction mixture was analyzed by gas chromatography. As a result, diphenyl carbonate was detected in an amount of 27 mmole, and methyl phenyl carbonate was detected in an amount of 50 mmole. Because the amount of methyl phenyl carbonate was not changed, the yield of diphenyl carbonate was able to calculated as 53% base on dimethyl carbonate. This reaction mixture was finely distilled using a Widmer distilling column. As a result of distillation, 3.5 g of diphenyl carbonate was thereby obtained and the purity was 98%.

EXAMPLE 16

Preparation of Phenyl 3,5-Dimethylbenzoate

A liquid reservoir having a volume of 10 ml was attached by pipes to the upper part of an autoclave made of titanium having an internal volume of 500 ml, to make an apparatus capable of condensing part of a gas phase. Into this autoclave were charged methyl 3,5-dimethylbenzoate 90 g (550 mmole), phenol 207 g (2200 mmole) and titanium tetraphenoxide/phenol adduct 2.8 g (5.5 mmole) in a state such that the phenol was melting. The autoclave was sealed and then cooled with ice. After sufficient cooling, the inner gas was evacuated with a vacuum pump. Then, the contents were heated and reacted at 230° C. Furthermore, during the reaction, the liquid held in the reservoir was continuously removed with a pump at a rate of 10 g per one hour. After reacting for three hours, the temperature of the reaction apparatus was adjusted to 200° C., and the pressure was gradually decreased to 100 mmHg. As with phenol, methyl 3,5-dimethylbenzoate was then stored in the liquid reservoir, and these substances were removed as needed. When the distillation was discontinued, the pressure was gradually decreased to 20 mmHg, and the apparatus was left standing to further remove the distilled liquid. Then, the contents were cooled and the internal liquid was sampled and analyzed. It was found to be a mixture of methyl 3,5-dimethylbenzoate (14 mmole) and phenyl 3,5-dimethylbenzoate (392 mmole).

Preparation of Carbonate

Without removing the reaction mixture from the reactor, dimethyl carbonate 17.7 g (196 mmole) was further added thereto. The air was then replaced by nitrogen. The autoclave was sealed, and the contents were reacted for one hour at 200° C. After completing the reaction, the reaction mixture was analyzed by gas chromatography. As a result, the yield of methyl phenyl carbonate was 23%, and the yield of diphenyl carbonate was 10% (the yield was based on dimethyl carbonate).

EXAMPLE 17

Preparation of Phenyl Benzoate

A Claisen head was attached to a flask having an internal volume of 1000 ml, and a receiver having a gage was attached to the Claisen head via a condenser to make a distillation apparatus. Into this apparatus were charged methyl benzoate 100 g (735 mmole), phenol 553 g (5876 mmole) and titanium tetraisopropoxide 2.1 g (7.4 mmole). The contents were reacted with stirring at 190° C. in a bath. The reaction was conducted at atmospheric pressure, and the methanol thus produced was removed together with phenol. After reacting for 4 hours, excess phenol was distilled at atmospheric pressure. The remaining phenol and methyl benzoate were distilled under vacuum to obtain phenyl benzoate. The boiling point was 140° C./4mmHg. The yield was 108 g (74% yield in terms of methyl benzoate).

Preparation of Carbonate

Into an autoclave made of SUS316 having an internal volume of 100 ml were charged phenyl benzoate 30 g (151 mmole) produced above, dimethyl carbonate 6.82 g (75.7 mmole) and gallium triisopropoxide 0.38 g (1.51 mmole). The pressure was elevated to 20 kg/cm$^2$ with nitrogen, and the contents were then reacted for two hours at 150° C. After completing the reaction, the reaction mixture was analyzed by gas chromatography. As a result, the yield of methyl phenyl carbonate was 25%, and the yield of diphenyl carbonate was 20%. Furthermore, methyl benzoate was produced as a by-product with a yield of 45% (the yield is given in terms of phenyl benzoate).

EXAMPLES 18–20

In the carbonate preparation step, the same procedures as in Example 17 were used, except that 1.51 mmole of the catalyst shown in the Table below was used in place of gallium triisopropxide. The results are shown below.

| Examples | Catalyst | MPC Yield | DPC Yield |
|---|---|---|---|
| 18 | Al(OEt)$_3$ | 23% | 15% |
| 19 | Sn(n-Bu)$_2$(OMe)$_2$ | 14% | 7% |
| 20 | SnO(n-Bu)$_2$ | 11% | 4% |

EXAMPLE 21

In Example 20, the same procedures as in Example 20 were used, except that the reaction temperature was 180° C., and the contents were reacted for three hours. As a result, the yield of methyl phenyl carbonate was 18%, and the yield of diphenyl carbonate was 21%. Furthermore, methyl benzoate was produced as a by-product with a yield of 39% (the yield is given in terms of phenyl benzoate).

While the invention has been described in detail and with reference to specific embodiments thereof, it will be apparent to one skilled in the art that various changes and modifications can be made therein without departing from the spirit and scope thereof.

What is claimed is:

1. A process for producing an aromatic carbonate which comprises reacting a dialkyl carbonate represented by general formula (1) with an aromatic carboxylic acid aryl ester represented by general formula (2) in the presence of a catalyst to produce an aromatic carbonate represented by one or both of general formulae (3) and (4):

R—OCOO—R     (1)

Ar'—COO—Ar     (2)

Ar—OCOO—R     (3)

Ar—OCOO—Ar     (4)

wherein R represents an alkyl group having from 1 to 4 carbon atoms, and Ar and Ar' each represents an unsubstituted phenyl group or a phenyl group substituted by a substituent selected from the group consisting of alkyl, alkoxy, aryl, aryloxy and a halogen atom.

2. The method for preparing an aromatic carbonate according to claim 1, which further comprises reacting an aromatic carboxylic acid alkyl ester represented by general formula (5) with an aromatic hydroxy compound represented by general formula (6) in the presence of a catalyst to produce an aromatic carboxylic acid aryl ester represented by general formula (2):

Ar'—COO—R     (5)

Ar—OH     (6)

wherein Ar, Ar' and R have the same meanings as defined in claim 1.

3. The method for preparing an aromatic carbonate according to claim 2, wherein an aromatic carboxylic acid alkyl ester is a by-product of the reaction of claim 1, and said aromatic carboxylic acid alkyl ester by-product is used as a reactant in the reaction of claim 2.

4. The method for preparing an aromatic carbonate according to claim 2, wherein the catalyst used to produce the aromatic carboxylic acid aryl ester represented by general formula (2) is the same catalyst used to produce the aromatic carbonate represented by one or both of general formulae (3) and (4).

5. The method for preparing an aromatic carbonate according to claim 3, wherein the catalyst used to produce the aromatic carboxylic acid aryl ester represented by general formula (2) is the same catalyst used to produce the aromatic carbonate represented by one or both of general formulae (3) and (4).

6. The process for producing an aromatic carbonate as claimed in claim 1, wherein the catalyst comprises at least one member selected from the group consisting of an alkoxide, an aryloxide, an alkyl substituted metal oxide and an acetyl acetonate of a metal selected from the group consisting of titanium, aluminum, gallium, tin, and yttrium, or an adduct thereof.

7. The process for producing an aromatic carbonate as claimed in claim 2, wherein the catalyst comprises at least one member selected from the group consisting of alkoxide, aryloxide, alkyl substituted oxide and acetylacetonate of metal selected from the group consisting of titanium, aluminum, gallium, tin and yttrium or an adduct thereof.

8. The process for producing an aromatic carbonate as claimed in claim 3, wherein the catalyst comprises at least one member selected from the group consisting of alkoxide, aryloxide, alkyl substituted oxide and acetylacetonate of metal selected from the group consisting of titanium, aluminum, gallium, tin and yttrium, or an adduct thereof.

9. The process for producing an aromatic carbonate as claimed in claim 6, wherein the catalyst is a compound represented by $Ti(OX)_4$ or $Ti(OX)_4 \cdot XOH$ where X is an alkyl group having 1 to 4 carbon atoms or an aryl group.

10. The process for producing an aromatic carbonate as claimed in claim 7, wherein the catalyst is a compound represented by $Ti(OX)_4$ or $Ti(OX)_4 \cdot XOH$ where X is an alkyl group having 1 to 4 carbon atoms or an aryl group.

11. The process for producing an aromatic carbonate as claimed in claim 8, wherein the catalyst is a compound represented by $Ti(OX)_4$ or $Ti(OX)_4 \cdot XOH$ where X is an alkyl group having 1 to 4 carbon atoms or an aryl group.

12. The process for producing an aromatic carbonate as claimed in claim 9, wherein the catalyst is a compound represented by $Ti(OAr)_4$ or $Ti(OAr)_4 \cdot ArOH$ where Ar is an aryl group.

13. The process for producing an aromatic carbonate as claimed in claim 10, wherein the catalyst is a compound represented by $Ti(OAr)_4$ or $Ti(OAr)_4 \cdot ArOH$ where Ar is an aryl group.

14. The process for producing an aromatic carbonate as claimed in claim 11, wherein the catalyst is a compound represented by $Ti(OAr)_4$ or $Ti(OAr)_4 \cdot ArOH$ where Ar is an aryl group.

15. The process for producing an aromatic carbonate as claimed in claim 12, wherein Ar is a phenyl group.

16. The process for producing an aromatic carbonate as claimed in claim 13, wherein Ar is a phenyl group.

17. The process for producing an aromatic carbonate as claimed in claim 14, wherein Ar is a phenyl group.

* * * * *

UNITED STATES PATENT AND TRADEMARK OFFICE
CERTIFICATE OF CORRECTION

PATENT NO. : 5,714,627
DATED : February 3, 1998
INVENTOR(S) : Masamichi MIZUKAMI et al It is certified that error(s) appears in the above-identified patent and that said Letters Patent is hereby corrected as shown below:

On the cover page, Item [57], line 1, change "process" to --method--.

In column 16, line 38, change "process" to --method--.

In column 17, line 18, change "process" to --method--;

line 25, change "process" to --method--; and line 31, change "process" to --method--.

In column 18, line 3, change "process" to --method--;

line 7, change "process" to --method--;

line 11, change "process" to --method--;

line 15, change "process" to --method--;

line 19, change "process" to --method--;

line 23, change "process" to --method--;

line 27, change "process" to --method--;

line 29, change "process" to --method--; and

UNITED STATES PATENT AND TRADEMARK OFFICE
CERTIFICATE OF CORRECTION

PATENT NO. : 5,714,627
DATED : February 3, 1998
INVENTOR(S) : Masamichi MIZUKAMI et al It is certified that error appears in the above-identified patent and that said Letters Patent is hereby corrected as shown below:

line 31, change "process" to --method--.

Signed and Sealed this

Twelfth Day of May, 1998

Attest:

BRUCE LEHMAN

Attesting Officer

Commissioner of Patents and Trademarks